US008845676B2

(12) United States Patent
Monstadt et al.

(10) Patent No.: US 8,845,676 B2
(45) Date of Patent: Sep. 30, 2014

(54) MICRO-SPIRAL IMPLANTATION DEVICE

(75) Inventors: Hermann Monstadt, Bochum (DE);
Achim Flesser, Mettman (DE); Ralf Hannes, Dortmund (DE)

(73) Assignee: Micro Therapeutics

( * ) Notice: Subject to any disclaimer, the term of this patent is extended or adjusted under 35 U.S.C. 154(b) by 2036 days.

(21) Appl. No.: 11/575,796

(22) PCT Filed: Sep. 22, 2004

(86) PCT No.: PCT/EP2004/010612
§ 371 (c)(1),
(2), (4) Date: Dec. 28, 2007

(87) PCT Pub. No.: WO2006/032291
PCT Pub. Date: Mar. 30, 2006

(65) Prior Publication Data
US 2008/0103585 A1    May 1, 2008

(51) Int. Cl.
*A61M 29/00* (2006.01)
*A61B 17/12* (2006.01)
(52) U.S. Cl.
CPC ....... *A61B 17/12022* (2013.01); *A61B 17/1215* (2013.01); *A61B 2017/12063* (2013.01)
USPC ............................. 606/200; 606/157; 606/194
(58) Field of Classification Search
USPC .......................................... 606/157, 194, 200
See application file for complete search history.

(56) References Cited

U.S. PATENT DOCUMENTS

| 3,174,851 A | 3/1965 | Buehler et al. |
| 3,753,700 A | 8/1973 | Harrison et al. |

(Continued)

FOREIGN PATENT DOCUMENTS

| DE | 10010840 | 9/2001 |
| DE | 10337000 A1 * | 3/2005 |

(Continued)

OTHER PUBLICATIONS

Henkes et al., Neurosurgery 54, No. 2, 268 (2004).

(Continued)

*Primary Examiner* — Victor Nguyen
*Assistant Examiner* — Kevin Everage
(74) *Attorney, Agent, or Firm* — Elizabeth A. O'Brien, Esq.

(57) ABSTRACT

The invention relates to a device for the implantation of microcoils (3, 7, 11, 12) into body cavities and blood vessels, in particular aneurysms, with said microcoils (3, 7, 11, 12) comprising wires forming a plurality of windings (4), at least one microcoil serving as occlusion helix (3) for the occlusion of the body cavity or blood vessel, and the device consisting of a catheter, one or several microcoils (3, 7, 11, 12) movably arranged in longitudinal direction within the catheter and at least one securing means (10) passing at least partially through the lumen (9) of the occlusion helix (3), with said securing means (10) being fixed in its end areas inside the microcoils (3, 7, 11, 12). Such a fixation of the securing means (10) is achieved in at least one end area by providing a frictional connection with the microcoil (3, 7, 11, 12) in such a manner that this connection is detachable from the microcoil (3, 7, 11, 12) when a certain tensile force acting on the securing means (10) is exceeded. In this way, a sudden breakage of the securing means (10) is avoided if too high a pull force is applied so that forces otherwise liberated cannot destroy the occlusion helix (3) or cause other damage in the blood vessel.

30 Claims, 4 Drawing Sheets

(56) References Cited

U.S. PATENT DOCUMENTS

| | | | |
|---|---|---|---|
| 3,834,394 | A | 9/1974 | Hunter et al. |
| 4,402,319 | A | 9/1983 | Handa et al. |
| 4,545,367 | A | 10/1985 | Tucci |
| 4,677,191 | A | 6/1987 | Tanaka et al. |
| 4,994,069 | A | 2/1991 | Ritchart et al. |
| 5,122,136 | A | 6/1992 | Guglielmi et al. |
| 5,226,911 | A | 7/1993 | Chee et al. |
| 5,256,146 | A | 10/1993 | Ensminger et al. |
| 5,304,194 | A | 4/1994 | Chee et al. |
| 5,354,295 | A | 10/1994 | Guglielmi et al. |
| 5,382,259 | A | 1/1995 | Phelps et al. |
| 5,382,260 | A * | 1/1995 | Dormandy et al. ........... 606/151 |
| 5,423,829 | A | 6/1995 | Pham et al. |
| 5,423,849 | A | 6/1995 | Engelson et al. |
| 5,443,478 | A | 8/1995 | Purdy |
| 5,476,472 | A | 12/1995 | Dormandy et al. |
| 5,485,496 | A | 1/1996 | Lee et al. |
| 5,522,822 | A | 6/1996 | Phelps et al. |
| 5,540,680 | A | 7/1996 | Guglielmi et al. |
| 5,549,624 | A | 8/1996 | Mirigian et al. |
| 5,582,619 | A | 12/1996 | Ken |
| 5,624,449 | A | 4/1997 | Pham et al. |
| 5,658,308 | A | 8/1997 | Snyder |
| 5,690,667 | A | 11/1997 | Gia |
| 5,700,258 | A | 12/1997 | Mirigian et al. |
| 5,746,734 | A | 5/1998 | Dormandy, Jr. et al. |
| 5,766,219 | A | 6/1998 | Horton |
| 5,833,705 | A | 11/1998 | Ken et al. |
| 5,843,118 | A | 12/1998 | Sepetka et al. |
| 5,851,206 | A | 12/1998 | Guglielmi et al. |
| 5,853,418 | A | 12/1998 | Ken et al. |
| 5,855,578 | A | 1/1999 | Guglielmi et al. |
| 5,891,128 | A | 4/1999 | Gia et al. |
| 5,891,192 | A | 4/1999 | Murayama et al. |
| 5,895,385 | A | 4/1999 | Guglielmi et al. |
| 5,911,731 | A | 6/1999 | Pham et al. |
| 5,919,187 | A | 7/1999 | Guglielmi et al. |
| 5,925,037 | A | 7/1999 | Guglielmi et al. |
| 5,928,226 | A | 7/1999 | Guglielmi et al. |
| 5,935,145 | A | 8/1999 | Villar et al. |
| 5,941,888 | A | 8/1999 | Wallace et al. |
| 5,944,714 | A | 8/1999 | Guglielmi et al. |
| 5,947,962 | A | 9/1999 | Guglielmi et al. |
| 5,947,963 | A | 9/1999 | Guglielmi |
| 5,976,126 | A | 11/1999 | Guglielmi et al. |
| 5,976,162 | A | 11/1999 | Doan et al. |
| 5,980,550 | A | 11/1999 | Eder et al. |
| 5,984,929 | A | 11/1999 | Bashiri et al. |
| 6,001,092 | A | 12/1999 | Mirigian et al. |
| 6,004,338 | A | 12/1999 | Ken et al. |
| 6,010,498 | A | 1/2000 | Guglielmi |
| 6,013,084 | A | 1/2000 | Ken et al. |
| 6,066,133 | A | 5/2000 | Guglielmi et al. |
| 6,077,260 | A | 6/2000 | Wheelock et al. |
| 6,083,220 | A | 7/2000 | Guglielmi |
| 6,123,714 | A | 9/2000 | Gia et al. |
| 6,143,007 | A | 11/2000 | Mariant et al. |
| 6,146,373 | A | 11/2000 | Cragg et al. |
| 6,156,061 | A | 12/2000 | Wallace et al. |
| 6,165,178 | A | 12/2000 | Bashiri et al. |
| 6,187,027 | B1 | 2/2001 | Mariant et al. |
| 6,193,728 | B1 | 2/2001 | Ken et al. |
| 6,221,066 | B1 | 4/2001 | Ferrera et al. |
| 6,231,586 | B1 | 5/2001 | Mariant |
| 6,280,457 | B1 | 8/2001 | Wallace et al. |
| 6,287,318 | B1 | 9/2001 | Villar et al. |
| 6,299,627 | B1 | 10/2001 | Eder et al. |
| 6,371,972 | B1 | 4/2002 | Wallace et al. |
| 6,423,085 | B1 | 7/2002 | Murayama et al. |
| 6,425,893 | B1 | 7/2002 | Guglielmi |
| 6,468,266 | B1 | 10/2002 | Bashiri et al. |
| 6,485,524 | B2 | 11/2002 | Strecker |
| 6,511,468 | B1 | 1/2003 | Cragg et al. |
| 6,558,367 | B1 | 5/2003 | Cragg et al. |
| 6,620,152 | B2 | 9/2003 | Guglielmi |
| 6,766,219 | B1 | 7/2004 | Hasey |
| 6,964,657 | B2 | 11/2005 | Cragg et al. |
| 7,070,607 | B2 | 7/2006 | Murayama et al. |
| 7,238,194 | B2 | 7/2007 | Monstadt et al. |
| 7,300,458 | B2 | 11/2007 | Henkes et al. |
| 7,323,000 | B2 | 1/2008 | Monstadt et al. |
| 7,422,569 | B2 * | 9/2008 | Wilson et al. ............... 604/113 |
| 7,485,317 | B1 | 2/2009 | Murayama et al. |
| 7,524,322 | B2 | 4/2009 | Monstadt et al. |
| RE41,029 | E | 12/2009 | Guglielmi et al. |
| 7,896,899 | B2 | 3/2011 | Patterson et al. |
| 8,267,955 | B2 | 9/2012 | Patterson et al. |
| 2002/0087184 | A1 | 7/2002 | Eder et al. |
| 2003/0014073 | A1 | 1/2003 | Bashiri et al. |
| 2003/0040733 | A1 | 2/2003 | Cragg et al. |
| 2003/0225365 | A1 | 12/2003 | Greff et al. |
| 2004/0002731 | A1 * | 1/2004 | Aganon et al. ............. 606/200 |
| 2004/0002733 | A1 | 1/2004 | Tech |
| 2004/0034378 | A1 * | 2/2004 | Monstadt et al. ............ 606/157 |
| 2004/0078050 | A1 | 4/2004 | Monstadt et al. |
| 2004/0098029 | A1 | 5/2004 | Teoh et al. |
| 2004/0170685 | A1 | 9/2004 | Carpenter et al. |
| 2005/0079196 | A1 | 4/2005 | Henkes et al. |
| 2005/0222603 | A1 | 10/2005 | Andreas et al. |
| 2006/0036281 | A1 | 2/2006 | Patterson et al. |
| 2006/0079926 | A1 | 4/2006 | Desai et al. |
| 2008/0045922 | A1 | 2/2008 | Cragg et al. |
| 2008/0051803 | A1 | 2/2008 | Monstadt et al. |
| 2008/0125855 | A1 | 5/2008 | Henkes et al. |
| 2008/0228215 | A1 | 9/2008 | Strauss et al. |
| 2008/0228216 | A1 | 9/2008 | Strauss et al. |
| 2008/0319532 | A1 | 12/2008 | Monstadt et al. |
| 2009/0254111 | A1 | 10/2009 | Monstadt et al. |
| 2010/0023105 | A1 | 1/2010 | Levy et al. |
| 2010/0030200 | A1 | 2/2010 | Strauss et al. |
| 2010/0049165 | A1 | 2/2010 | Sutherland et al. |
| 2010/0076479 | A1 | 3/2010 | Monstadt |
| 2011/0118777 | A1 | 5/2011 | Patterson et al. |
| 2012/0116442 | A1 | 5/2012 | Monstadt et al. |

FOREIGN PATENT DOCUMENTS

| | | | |
|---|---|---|---|
| EP | 0368571 | A2 | 5/1990 |
| EP | 0792623 | A | 9/1997 |
| EP | 0800791 | | 10/1997 |
| WO | WO-99/40852 | A1 | 8/1999 |
| WO | WO 99/51151 | | 10/1999 |
| WO | WO9951151 | A | 10/1999 |
| WO | WO 2006032291 | A1 * | 3/2006 |

OTHER PUBLICATIONS

Middleton, J.C. & Tipton, A.J. Synthetic biodegradable polymers as orthopedic devices, Biomaterials 21, 2335-46 (2000).

* cited by examiner

MICRO-SPIRAL IMPLANTATION DEVICE

BACKGROUND OF THE INVENTION

The invention relates to a device for the implantation of microcoils into body cavities and blood vessels, in particular aneurysms, with the microcoils comprising wires forming a plurality of windings, at least one microcoil serving as occlusion helix for the occlusion of the body cavity or blood vessel, and the device consisting of a catheter, one or several microcoils movably arranged in longitudinal direction within the catheter and at least one securing means passing at least partially through the lumen of the occlusion helix, with the securing means being fixed in its end areas inside the microcoils. Furthermore, the invention relates to an occlusion helix to be used in connection with the aforedescribed device.

The use of endovascular techniques for the occlusion of body cavities or vessels such as arteries, veins, fallopian tubes or vascular deformities (for example, vascular aneurysms) is known in the art. In this case, the occlusion helix is usually introduced by means of an endovascular insertion wire through a catheter into the cavity to be occluded and deposited therein.

Before placement may commence the occlusion helixes are maneuvered with the help of the catheter through the blood vessel system and, at the target site, advanced out of the catheter and into the cavity to be occluded. Ideally, the separation/severance of the helix follows these steps. In the event of a wrong placement of the occlusion helix or if too large an occlusion helix has been selected for the area to be occluded the helix must then be repositioned or completely retracted into the catheter to subsequently enable such an occlusion helix to be correctly positioned or a correctly sized helix to be placed in position. Maneuvers of this kind involve risks in that parts of the helix are pulled apart and elongated due to the tensile or torsional stresses applied, and in this way become plastically deformed irreversibly, are torn off or broken which may give rise to life-threatening embolism.

To minimize this danger it has been known, inter alia from the European Patent Specification EP 0 792 623 B1, to provide for a polymeric, non-extensible element passing through the lumen of the occlusion helix, the element being permanently attached to the occlusion helix at two places at least. Such a design enables an occlusion helix to be repositioned or retracted into the catheter in such a manner that it is not pulled apart and elongated so that an irreversible deformation can be avoided.

However, this prior-art technique has the disadvantage in that the polymer thread may suddenly break in the event that too high a retraction force is exerted. In such a case the entire tensile load suddenly acts on the occlusion helix itself which may cause not only deformation but may even lead to occlusion helix breakage. Since such a break of the polymer thread may occur all of a sudden the detrimental effects caused in the blood vessel may be considerable and can hardly be controlled.

In view of the problems described above it is therefore the object of the invention to provide a device for the implantation of occlusion helixes that permit a higher degree of safety to be achieved for patients when occlusion helixes are inserted and placed than can be brought about by prior-art means.

SUMMARY OF THE INVENTION

According to the invention this objective is reached by providing a device of the kind first mentioned above wherein, in order to achieve a frictional connection, the securing means is fixed in the a microcoil at least in one end area in such a manner that this connection is detachable from the microcoil when a certain tensile force acting on the securing means is exceeded.

By providing only a frictional but not a permanent connection in one end area of the securing means it is ensured that the securing means in this end area is retained in the microcoil by means of frictional forces only. As is doubtlessly possible without difficulty for persons skilled in the art the frictional connection can be designed to involve frictional forces lower than the pull force that must act on the securing means in order to bring about a failure or breakage. On the other hand, the frictional force must be set high enough to enable a retraction and repositioning of the occlusion helix to be performed under normal conditions without problems. In the event the tensile force increases to such an extent that the securing means must be expected to break, the securing means is released at its point of attachment within the microcoil and pulls out of the same so that the frictional connection becomes detached and a failure/breakage of the securing means is avoided. Moreover, the frictional connection will not become detached abruptly as in the case of a failure of the securing means but gradually so that no sudden forces are exerted and permitted to cause negative effects as may be encountered as described with design configurations provided for by prior-art methods. The implantation device provided for by the present invention will cause an "overload slipping clutch" effect.

The frictional connection between the securing means and a microcoil may be established by various methods. One possible design method provides for the securing means to extend between individual or several windings of a microcoil in such a manner that it becomes clamped between the windings. In this case the securing means extends through several gaps between the windings of a microcoil. The strength of the frictional connection can be adjusted via the number of the clamping instances in the gaps between windings provided for the securing means. The securing means in this case may be clamped between the windings on opposites sides of the microcoil resulting in the securing means to cross the microcoil lumen several times in this end area, but may as well extend through the windings of the microcoil on one side only. Another conceivable method of bringing about the frictional connection also provides for the securing means to be wrapped in its end area once or several times around the wire forming the windings of the microcoil so as to produce loops so to speak around the wire forming the microcoil.

Basically, the microcoil to which the securing means is attached may be the occlusion helix itself or microcoils connected to the occlusion helix. In the latter case, the securing means is only indirectly attached to the occlusion helix which offers advantages in that this embodiment is particularly cost effective because customary occlusion helixes may be used for its manufacture. Microcoils attached to the securing means may be inserted into the occlusion helix with the help of customary methods. To connect the microcoil to the occlusion helix methods sufficiently known to persons skilled in the art are suited such as welding, soldering, bonding or mechanical joining processes. Typically, a smaller microcoil is inserted into the occlusion helix both on the distal and on the proximal end with the securing means being attached via the microcoils so inserted.

In accordance with such a conceivable embodiment of the invention at least one additional microcoil is placed in a microcoil serving as occlusion helix, with the outside diameter of the former microcoil corresponding to the inside diameter of the occlusion helix, and the securing means being clamped in at least one end area between the windings of the inner microcoil and the windings of the occlusion helix to enable a frictional connection to be established in this way. An inner microcoil placed in the proximal area may at the same time serve as severance element for the electrolytic detachment of the occlusion helix. The method of electrolytic severance of occlusion helixes is sufficiently known to competent persons skilled in the art and offers many advantages in terms of practicability, safety and cost-effectiveness over other techniques known from prior-art and aimed at separating occlusion helixes. For this purpose, one or several separately spaced electrolytically corrodible locations are provided in the device, expediently within the occlusion helix, with the locations in conjunction with an electrically insulating catheter and a voltage source as well as a cathode usually is positioned on the body surface permitting detachment or severance by electrolytic corrosion. The occlusion helix in this case serves as anode. Aside from this, also prior-art devices are known which provide for the detachment point being arranged in the guide wire.

It is particularly expedient if the occlusion helix, as is known from DE 100 10 840 A1, has several electrolytically corrodible locations, with a securing means being arranged in each segment of the occlusion helix situated between these locations, the securing means preferably extending from one end to the other end of each segment. This embodiment enables the placement of variably sizable lengths of occlusion helixes and at the same time ensures that each individual segment arranged between the electrolytically corrodible points is secured so that a maximum degree of safety is achieved with respect to pre-venting the occlusion helix from being torn off.

Aside from the possibility to clamp the securing means between the windings of the occlusion means and the windings of a microcoil arranged inside the occlusion helix there is also an alternative wherein a thickening element is provided in the end area of the occlusion helix, the outside diameter of which corresponds to the inside diameter of the occlusion helix, and the securing means is clamped between the windings of the occlusion helix and the thickening element. A variety of shapes are conceivable for such a thickening element to be used for the fixation of the securing element with the help of a frictional connection by way of a kind of plug inserted into the occlusion helix.

To bring about the "overload slipping clutch" effect as provided for by the invention it will be sufficient to attach the securing means in one of its end areas to a microcoil by means of a frictional connection whereas the securing means in its other end area is permanently connected to a microcoil. Since from a manufacturing point of view a permanent connection between securing means and microcoil can be produced more easily such a solution is preferred wherein the securing means may be permanently attached both at the proximal and at the distal end of a microcoil. The attachment at the distal end in this case will be less problematic due to manufacturing reasons. It is, of course, also possible to attach the securing means in a microcoil in both end areas by means of a frictional connection so that the securing means can be detached from the microcoil both proximally as well as distally if the pull force acting on the device exceeds a certain limit.

To establish a permanent connection between securing means and microcoil customary methods known from prior-art techniques can be applied such as, for example, gluing, fusing or soldering, depending on the material employed for the securing means. Another way of fixing the securing means at the distal end is to attach it to a thickening element located at the distal end, the thickening element being arranged distally in the microcoil and designed to prevent the securing means from sliding through the microcoil by providing for the diameter of the thickening element to be greater than the inner diameter of the microcoil. The thickening element may, for example, have the form of a sphere or ball. In this manner, a detachment of the securing means from the distal end is prevented without having established a direct, permanent connection between microcoil and securing means.

Moreover, optional combinations of conceivable frictional and permanent connections at the proximal and distal end are possible in the framework of the invention.

As per a particularly preferred embodiment the securing means is a polymer thread or a polymer thread bundle. Such a polymer thread has adequate flexibility so that it can be passed through the gaps between the windings of a microcoil or around the windings of a microcoil. What is more, there are almost no limits to design such a polymer thread to be as thin as required for a given use which makes it possible for the securing means to be used with any conceivable occlusion helixes, in particular those used for intracranial applications. Due to the fact that the gaps between windings of a microcoil are in the range of just 0.008 and 0.01 mm it is an absolute must to provide for securing means that are designed to be as thin as possible.

As polymers numerous biocompatible materials may be employed such as, for example, polyesters, i.e. Dacron, polyamides, in particular nylon, polyolefins, polypropylenes, polybutylenes etc. Another possibility in this context is to incorporate individual metal fibers into the polymer thread with a view to increasing the breaking strength in this manner. Although it is preferred to use polymer threads as securing means the scope of the present invention does by no means exclude the use of other securing means, in particular those on metal basis.

For the production of the polymer threads the use of polyamides, particularly nylon, has turned out to offer special advantages. When using polymer threads as securing means an additional effect may achieved if the polymer threads have thrombogeneous properties. The provision of thrombogeneous threads in occlusion means is basically known in the framework of prior-art techniques, for example from the European Patent Specification EP 0 800 791 A1 or the U.S. Pat. No. 5,382,259. Fibers having a thrombogeneous effect promote the development of thrombi in the body cavity to be occluded, particularly in aneurysms, and in this way make sure the aneurysm can be effectively occluded. A further improvement can be achieved by coating the polymer thread or the securing means and/or the occlusion helix with collagen.

To enable the polymer thread to produce the desired effect it is considered expedient if it projects outwardly from the occlusion helix at one or several locations. The ends of the polymer thread may project from the occlusion helix especially if the polymer threads are clamped in the end area between the windings of the occlusion helix. If the polymer thread extends several times to and fro between the windings several locations will be created in this way where the polymer thread projects from the microcoil which results in the thrombogeneous effect to increase.

Aside from the provision of locations in the end area of the occlusion helix where the polymer thread projects outwardly from it, it is also possible for the polymer thread to project outwardly from the occlusion helix by producing loops at one or several locations between the proximal and distal end of the occlusion helix. Such a loop may extend through the gap between two windings or may also wrap around one or several windings. It is basically possible for the polymer thread to partly project outwardly along the entire length of the occlusion helix and the polymer thread so that it can effectively produce its thrombogeneous effect in this manner. To rule out that such a loop is drawn back into the lumen of the microcoil as soon as a tensile force is exerted on it, it is considered expedient to additionally wrap the polymer thread, adjacent to the loops, around individual windings of the occlusion helix and in this way further secure the position of the loop. Accordingly, the polymer thread may not only fulfill its inventive purpose as securing means but produce a thrombogeneous effect as well.

There is another possibility to combine the inventive effect with the thrombogeneous effect of polymer threads in that individual, shorter polymer threads are wrapped around the securing means extending through the lumen of the occlusion helix in longitudinal direction, with the ends of the threads projecting outwardly from the occlusion helix. The securing means together with the shorter polymer threads may also be heated up which causes the securing means and/or the shorter polymer threads to soften so that in this way bonding/gluing occurs. This is thus to be seen as a matter of fusing the polymer threads onto the inner securing means. There is another possibility of connecting the shorter polymer threads with the internally extending securing means in that the inner securing means is provided with an adhesive coating that fixes and retains the polymer threads. The two methods last described may of course also be combined. It is deemed particularly advantageous to initially wrap the shorter polymer threads around the securing means and subsequently heat them up to bring about the adhesive effect, and/or wrap the polymer threads around a securing means provided with an adhesive coating.

The positions of the polymer threads are further secured in that the threads, in their end area, extend through the occlusion helix and are appropriately clamped between the windings thereof. The fixation of polymer threads capable of producing a thrombogeneous effect is of special significance because polymer threads that have detached may cause the formation of thrombi in undesirable places and, besides, are difficult to locate. Naturally, the development of thrombi in important blood vessels involves grave health risks for the patients concerned.

Typically, a polymer thread consists of individual fibers which are spun or twisted together. To bring about the thrombogeneous effect it will, therefore, be sufficient if only some of the fibers of a polymer thread project outwardly from the occlusion helix whereas other fibers practically over their entire length extend through the lumen of the occlusion helix to fulfill their inventive purpose as securing means. Individual fibers shorter than the polymer thread itself may also be incorporated into the polymer thread, with the ends of the shorter fibers projecting outwardly from the occlusion helix. In the event individual fibers are available in sufficient number the occlusion means may be provided with outwardly projecting thrombogeneous fibers practically along its entire length. The thrombogeneous fibers in this case as well are secured and fixed in place by passing them through the gaps between the windings of the occlusion helix.

Individual fibers projecting outwardly from the occlusion helix may also be stuck or fused onto the securing means instead of being spun into the polymer thread which serves as securing means. Basically, this may also be done in case the securing means, for example, consists of a metal thread instead of a polymer thread. To enable fibers to be fused it is considered expedient to use for the fibers a thermoplastic material such as polyamides.

Preferably, the securing means of the device according to the invention is a little longer than the particular portion of the microcoil along which it extends. The length of the securing means established in this manner results in a less rigid arrangement in spite of the attachment or fixation inside the microcoil so that in the absence of external forces being exerted the securing means in the microcoil is not subjected to tensile stresses and the flexibility of the microcoil is not restricted. The securing means may as well extend over the entire length of the occlusion helix from the proximal to the distal end without having to make sacrifices in movability and flexibility so that in this way the entire occlusion helix can be secured by preventing it from being torn off. Since the distal tip of an occlusion helix is subjected to particularly high stresses when the helix is placed into a blood vessel the securing means should in fact extend up to the distal tip section of the occlusion helix.

Due to the low traumatizing risks involved platinum and platinum alloys, in particular platinum-iridium alloys, have proven their worth in the manufacture of microcoils and occlusion helixes. The occlusion helix may also be preformed into a superimposed structure which it only assumes in the aneurysm after it has been released from the catheter. In this way the aneurysm is filled up particularly effectively. Preferably, an insertion aid in the form of a guide wire is attached proximally to the occlusion helix.

Aside from a device for the implantation of microcoils into body cavities and blood vessels the invention also relates to the occlusion helix itself which is used in conjunction with the inventive device.

BRIEF DESCRPITION OF THE DRAWING

The invention is now described in detail as follows with reference being made to the figures showing the respective embodiments.

Figure 3:
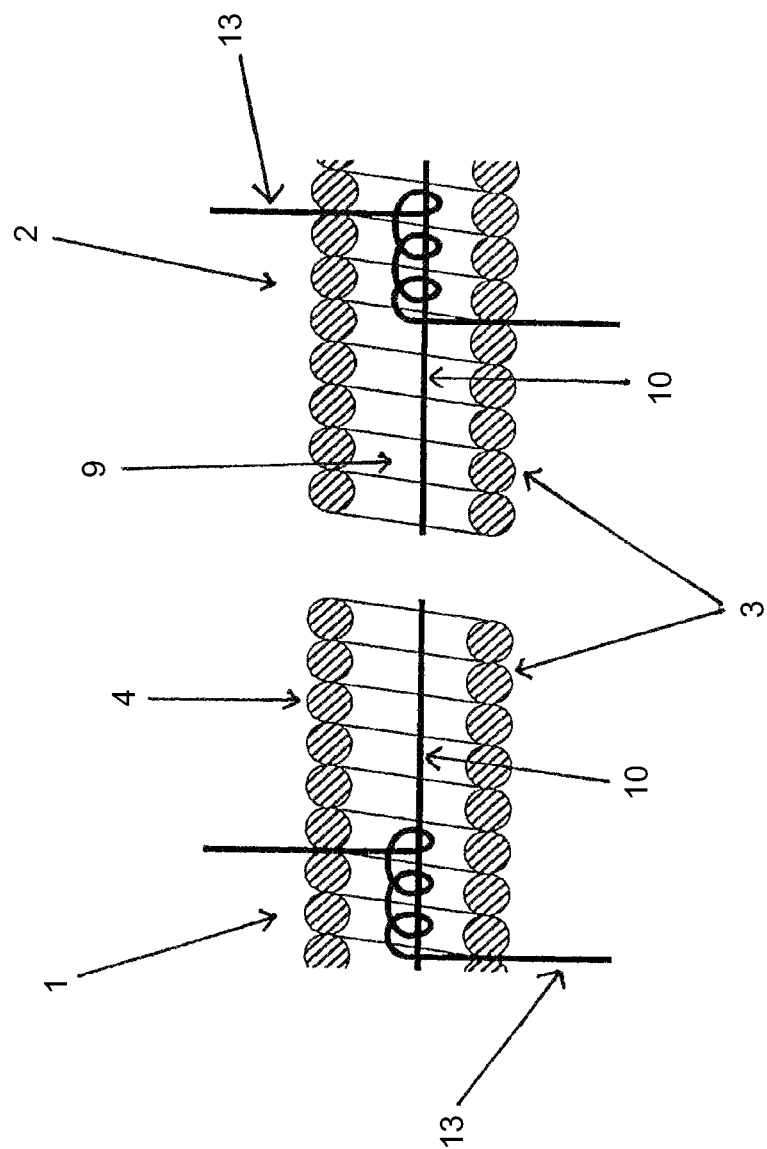
Figure 4:
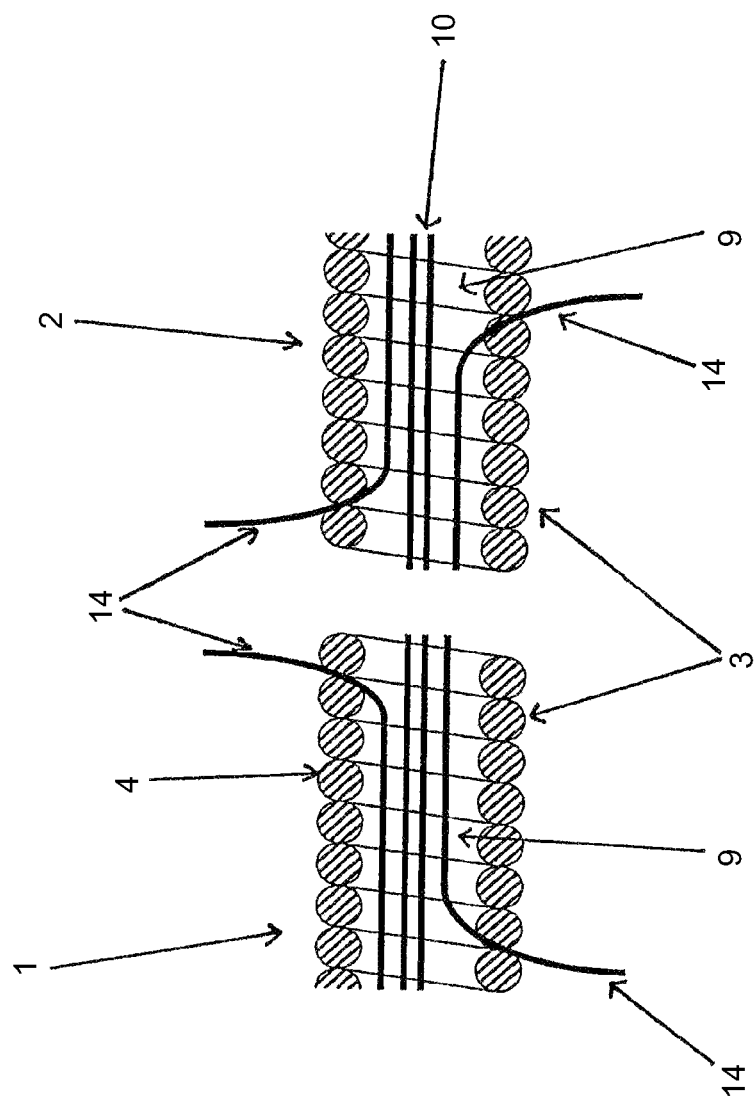

FIG. 3 is a longitudinal section of an inventive device (without catheter, distal tip and severance element) as side view showing the proximal and distal area in accordance with a third embodiment of the invention; and FIG. 4 is a longitudinal section of an inventive device (without catheter, distal tip and severance element) as side view showing the proximal and distal area in accordance with a fourth embodiment of the invention.

DETAILED DESCRIPTION OF PREFERRED EMBODIMENTS

Figure 1:
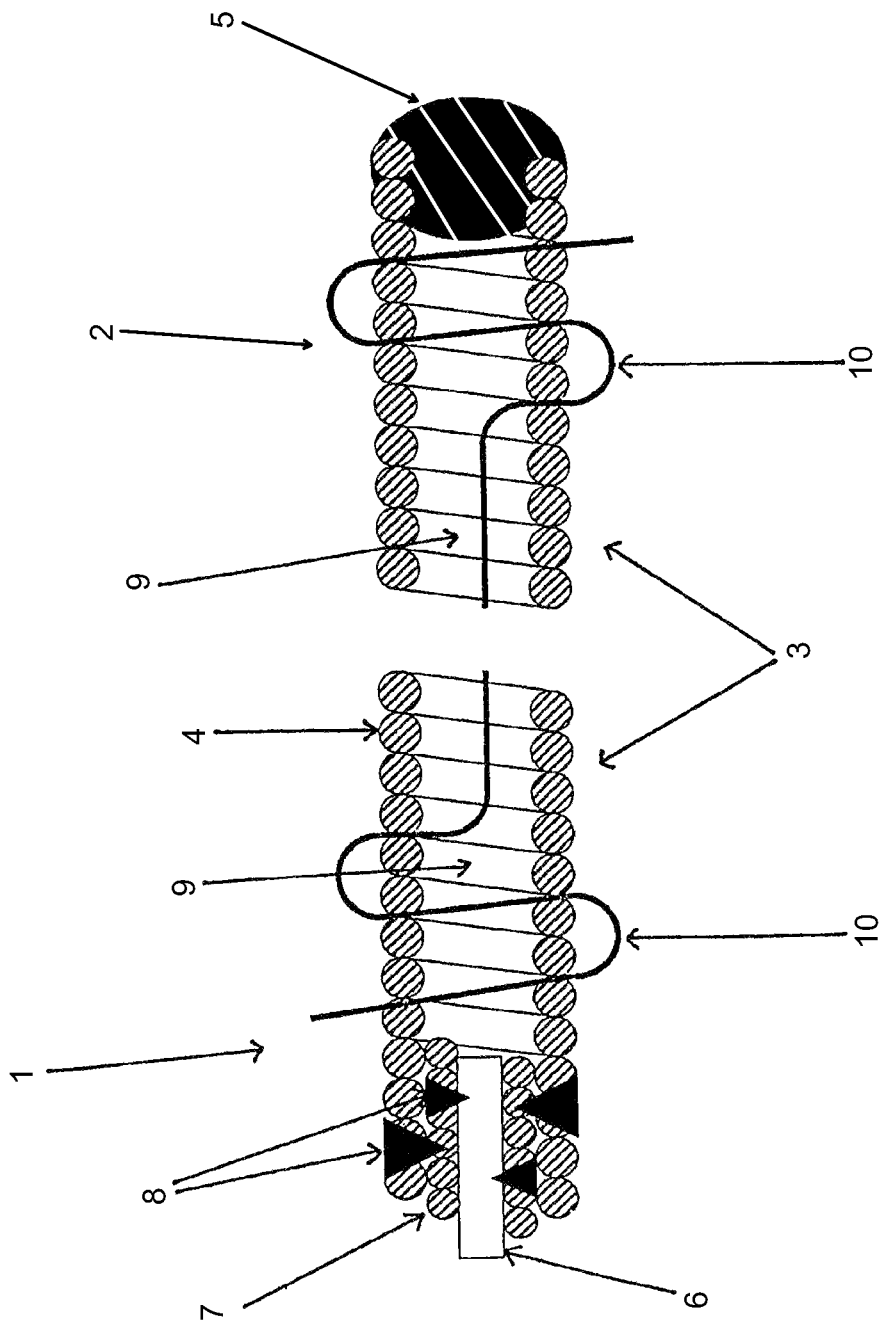
FIG. 1 is a longitudinal section of an inventive device (without catheter) as side view showing the proximal and distal area in accordance with a first embodiment of the invention.

From FIG. 1 the proximal area 1 and the distal area 2 of an occlusion helix 3 can be seen shown as a longitudinal section. The occlusion helix 3 shown here consists of a wire comprising a plurality of windings 4. The distal tip 5 of the occlusion helix 3 is rounded with a view to minimizing aneurysm traumatizing risks. Proximally to the occlusion helix 3 there is a severance element 6 which extends through a microcoil 7 additionally incorporated into the occlusion helix 3. The connection between the additional microcoil 7 and the occlusion helix 3 and between severance element 6 and additional microcoil 7 is made by providing joining points 8, for which purpose various techniques may be employed such as soldering, welding, bonding or mechanical joining methods. The severance element 6 is designed so as to be electrolytically corrodible to enable the occlusion helix 3 by applying a voltage to be released and placed into the aneurysm.

A polymer thread extends through the lumen 9 of the occlusion helix 3 in longitudinal direction and serves as securing means 10, with the thread extending to and fro between the windings 4 of the occlusion helix 3 in several places both in the proximal and in the distal end areas in such a manner that it is secured within the occlusion helix 3 by means of a frictional connection. However, in the event a certain pull force is exceeded the polymer thread 10 may slip out of the windings 4. The force to be overcome to bring about this slipping movement may be adjusted by way of the number of runs of the polymer thread 10 provided between the individual windings 4 of the occlusion helix 3. The maximum tensile or pull force of course increases if the polymer thread 10 extends through the windings 4 more frequently. Moreover, the polymer thread 10 in its end areas projects from the occlusion helix 3 several times which enables it to produce a thrombogeneous effect.

Figure 2:
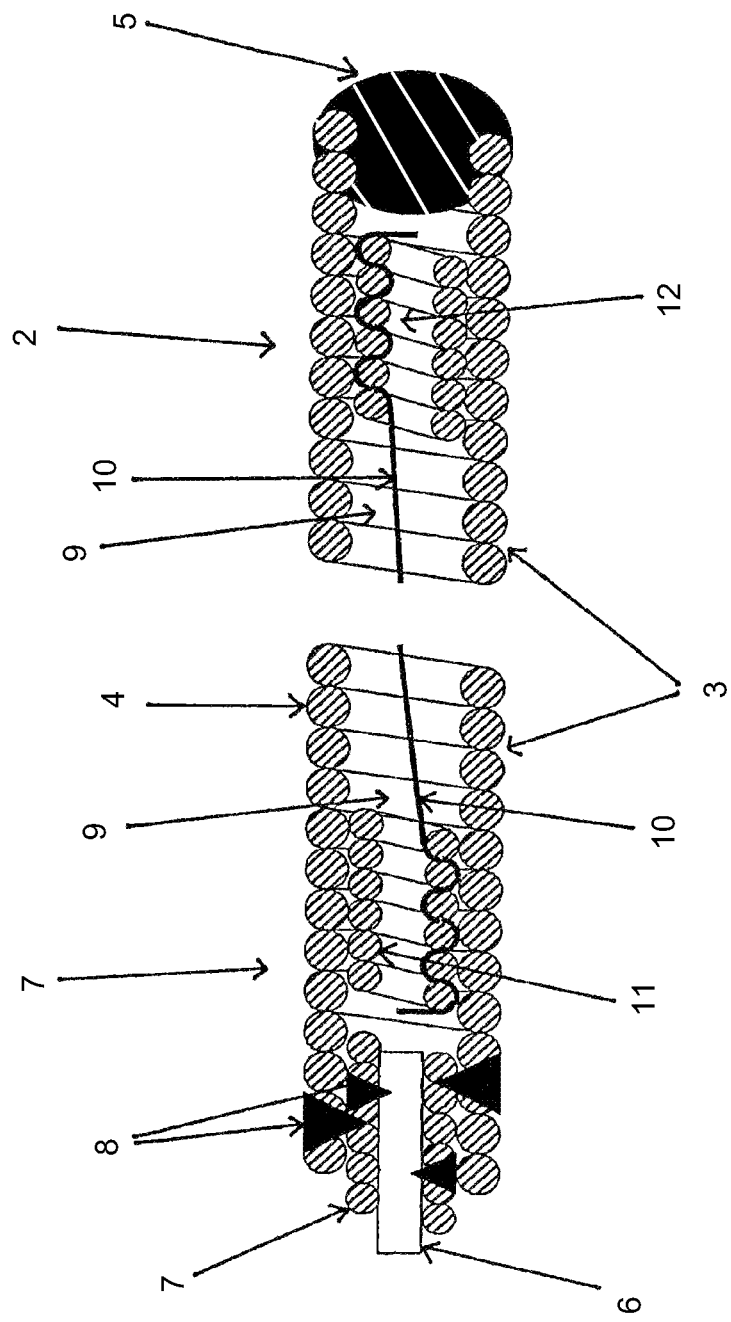
FIG. 2 is a longitudinal section of an inventive device (without catheter) as side view showing the proximal and distal area in accordance with a second embodiment of the invention.

FIG. 2 shows an alternative embodiment of the invention, wherein both in the proximal area 1 and in the distal area 2 of the occlusion helix 3 an additional microcoil 11, 12 has been incorporated, the outer diameter of which corresponding to the inner diameter of the occlusion helix 3. The inner microcoils 11, 12 may be threaded into the occlusion helix 3 and secured by techniques such as laser welding, soldering or bonding to the occlusion helix 3. The polymer thread serving as securing means 10 is clamped both in the distal and in the proximal area between the windings of the inner microcoil 11, 12 and the windings 4 of the occlusion helix 3 and in this manner secured and fixed with the help of a frictional connection. In this case the polymer thread 10 does not project outwardly from the occlusion helix 3 so that an additional thrombogeneous effect cannot be produced. When making use of additional microcoils 11, 12 it is, of course, also possible to provide for an arrangement wherein the polymer thread 10 projects from occlusion helix 3. Furthermore, it is also possible for the inner microcoil 11, 12 to be configured in such a manner that it is connected both with the polymer thread 10 and the severance element 6 by combining the inner microcoils 7 and 11 and 7 and 12.

In accordance with a third embodiment of the invention as illustrated in FIG. 3 the securing means 10 extends through the lumen 9 both in the proximal area 1 and in the distal area 2 of the occlusion helix 3. To enable the inventive effect to be achieved the securing means 10 is secured in the occlusion helix 3 in the proximal and/or distal end area by way of a frictional connection. Moreover, around the securing means 10 individual, shorter polymer threads 13 are wound, the ends of which are permitted to outwardly project from the occlusion helix 3. The projecting polymer threads 13 serve the purpose of bringing about a thrombogeneous effect within the body cavities to be occluded, in particular in aneurysms. In the end areas the polymer threads 13 extend through the windings 4 of the occlusion helix 3 so that they become clamped between the windings 4 and in this way are fixed and secured.

Advantageously, the polymer threads 13 are additionally connected with the securing means 10 in that they are heated up together with the securing means 10 which causes softening of the polymer threads 13 and/or the securing means 10, which may also be a polymer thread, so that a bonding effect finally occurs. There is another possibility of fixing the polymer threads 13 to the securing means 10 in that the securing means 10 is provided with an adhesive coating. For purposes of clarity, the polymer threads 13 in FIG. 3 are shown to merely wrap around the securing means 10 with a permanent fixation not having been illustrated.

As has been shown in FIG. 4, in a further embodiment as well the securing means 10 extends through the lumen 9 of the occlusion means 3 between the proximal area 1 and the distal area 2. For the purpose of producing the inventive effect the securing means 10 is frictionally connected with the occlusion helix 3 in at least one end area. In this case the securing means 10 is a polymer thread which consists of individual fibers. Here, some of the fibers extend virtually over their entire length through the lumen 9 of the occlusion helix 3, whereas other fibers 14 are shorter than the overall length of the securing means 10, with the ends of the other fibers projecting outwardly from the occlusion helix 3. The projecting fibers 14 also serve the purpose of achieving a thrombogeneous effect. The fixation of the thrombogeneous fibers 14 is brought about by passing them through the windings 4 of the occlusion helix 3 such that the fibers 14 in their end area are quasi clamped between the windings 4. It is, furthermore, considered expedient to incorporate the thrombogeneous fibers 14 into the securing means 10 by joining them, using spinning or twisting methods, with the polymer thread forming the securing means 10. Alternatively, the fibers 14 may also be bonded or fused onto the securing means 10.

To illustrate the principle of the invention more clearly, joining the fibers 14 to the securing means 10 by twisting has not been shown in FIG. 4.

What is claimed is:

1. A device for the implantation of microcoils into body cavities and blood vessels, in particular aneurysms, said microcoils comprising wires forming a plurality of windings, at least one microcoil serving as an occlusion helix for occlusion of the body cavity or blood vessel, the device comprising:
    a catheter;
    a first microcoil serving as the occlusion helix movably arranged within the catheter in a longitudinal direction;
    a second microcoil placed in the first microcoil, with an outside diameter of the second microcoil corresponding to an inside diameter of the first microcoil;
    securing means passing at least partially through a lumen of the occlusion helix, said securing means being fixed at end areas thereof inside the first microcoil, the securing means being clamped in at least one end area of the first microcoil between windings of the second microcoil and windings of the first microcoil, wherein the securing means in order to achieve a frictional connection is fixed in the first microcoil at least at one end area of the first microcoil in such a manner that the securing means is detachable from the first microcoil when a tensile force acting on the securing means overcomes a frictional force of the frictional connection.

2. The device according to claim 1, characterized in that the securing means passes in one end area in at least one turn around the wire forming windings of the first microcoil.

3. The device according to claim 1, characterized in that the securing means is fixed in two end areas in the first microcoil by means of a frictional connection.

4. The device according to claim 1, characterized in that the securing means is frictionally connected at a distal end area and at a proximal end area to a microcoil.

5. The device according to claim 1, characterized in that the securing means is permanently connected at a proximal end area and frictionally connected at a distal end area to a microcoil.

6. The device according to claim 5, characterized in that the securing means is attached at the distal end to a thickening element arranged distally of a microcoil with said element preventing passage through the microcoil.

7. The device according to claim 1, characterized in that the securing means is one of a polymer thread or a polymer thread bundle.

8. The device according to claim 7, characterized in that the polymer thread has a thrombogeneous effect.

9. The device according to claim 8, characterized in that the polymer thread comprises a polyamide.

10. The device according to claim 7, characterized in that one of the securing means and the occlusion helix is provided with a collagen coating.

11. The device according to claim 7, characterized in that the polymer thread projects outwardly from the occlusion helix.

12. The device according to claim 11, characterized in that the polymer thread projects outwardly from and produces loops on the occlusion helix between proximal and distal ends of the occlusion helix.

13. The device according to claim 12, characterized in that adjacent to the loops the polymer thread is wrapped around individual windings of the occlusion helix.

14. The device according to claim 13, characterized in that one or more first polymer threads are wrapped around a second polymer thread with ends of said one or more first polymer threads projecting outwardly from the occlusion helix.

15. The device according to claim 14, characterized in that the second polymer thread is provided with an adhesive coating causing the one or more first polymer threads to be bonded to the second polymer thread with ends of said one or more first polymer threads projecting outwardly from the occlusion helix.

16. The device according to claim 15, characterized in that the one or more first polymer threads are fused onto the second polymer thread with the ends of said one or more first polymer threads projecting outwardly from the occlusion helix.

17. The device according to claim 16, characterized in that the one or more first polymer threads or second polymer thread consists of individual fibers.

18. The device according to claim 17, characterized in that some fibers of the one or more first polymer threads or second polymer thread project outwardly from the occlusion helix whereas other fibers of the one or more first polymer threads or second polymer thread pass through the lumen of the occlusion helix along the entire length.

19. The device according to claim 17, characterized in that individual fibers of the one or more first polymer threads or second polymer thread are shorter than the one or more first polymer threads or second polymer thread in its entirety and wherein individual fiber ends project outwardly from the occlusion helix.

20. The device according to claim 1 wherein individual fibers are glued to or fused onto the securing means and project outwardly from the occlusion helix.

21. The device according to claim 1 wherein the occlusion helix has plural locations that are electrolytically corrodible, and wherein in segments of the occlusion helix a securing means is arranged between said locations.

22. A device for the implantation of microcoils into body cavities and blood vessels for occlusion of the body cavity or blood vessel, the device comprising:
a catheter;
a first microcoil movably arranged within the catheter in a longitudinal direction;
a thickening element placed in the first microcoil, an outside diameter of said thickening element corresponding to an inside diameter of the first microcoil; and
securing means passing at least partially through a lumen of the first microcoil, said securing means being fixed at end areas thereof inside the first microcoil, said securing means being clamped in at least one end area between windings of the first microcoil and the thickening element, wherein the securing means in order to achieve a frictional connection is fixed in the first microcoil at least in one end area in such a manner that the securing means is detachable from the first microcoil when a tensile force acting on the securing means overcomes a frictional force of the frictional connection.

23. The device according to claim 22, characterized in that the securing means is fixed in two end areas in the first microcoil by means of a frictional connection.

24. The device according to claim 22, characterized in that the securing means is frictionally connected at a distal end area and at a proximal end area to a microcoil.

25. The device according to claim 22, characterized in that the securing means is one of a polymer thread or a polymer thread bundle.

26. A device for the implantation of microcoils into body cavities and blood vessels for occlusion of the body cavity or blood vessel, the device comprising:
a catheter;
a microcoil movably arranged within the catheter in a longitudinal direction and comprising proximal and distal end areas; and
a securing member passing at least partially through a lumen of the microcoil, said securing member extending continuously between (i) a proximal end portion thereof, permanently connected to the proximal end area, and (ii) a distal end portion thereof, frictionally connected to the distal end area, wherein the distal end portion is clamped against windings of the microcoil in such a manner that the distal end portion is detachable from the microcoil when a tensile force acting on the securing member overcomes a frictional force of the frictional connection.

27. The device according to claim 25, characterized in that the securing member is attached at the distal end to a thickening element arranged distally of a microcoil with said element preventing passage through the microcoil.

28. A device for the implantation of microcoils into body cavities and blood vessels for occlusion of the body cavity or blood vessel, the device comprising:
a catheter;
a microcoil movably arranged within the catheter in a longitudinal direction and comprising a proximal end area;
securing means passing at least partially through a lumen of the microcoil and comprising at least one polymer thread, wherein a polymer thread projects outwardly from the microcoil and produces loops on the microcoil between proximal and distal ends of the microcoil, the polymer thread being wrapped around individual windings of the microcoil adjacent to the loops, wherein one or more polymer threads are wrapped around a given polymer thread, the given polymer thread being provided with an adhesive coating causing the one or more polymer threads to be bonded to the given polymer thread with ends of the one or more polymer threads projecting outwardly from the microcoil, the securing means comprising (i) a proximal end portion, coupled to the proximal end area, and (ii) a distal end portion, clamped against windings of the microcoil in such a manner that the distal end portion is detachable from the microcoil when a tensile force acting on the securing means overcomes a frictional force of the frictional connection.

29. The device according to claim 28, characterized in that the polymer thread comprises individual fibers.

30. A device for the implantation of microcoils into body cavities and blood vessels for occlusion of the body cavity or blood vessel, the device comprising:
  a catheter;
  a microcoil movably arranged within the catheter in a longitudinal direction; and
  a securing member passing at least partially through a lumen of the microcoil, said securing member extending continuously between (i) a proximal end portion thereof, coupled to a proximal end area of the microcoil, and (ii) a distal end portion thereof, clamped against windings of the microcoil, in order to achieve a frictional connection such that the distal end portion is detachable from the microcoil when a tensile force acting on the securing member overcomes a frictional force of the frictional connection,
  wherein the microcoil has plural locations that are electrolytically corrodible, and wherein in segments of the microcoil the securing member is arranged between said locations.

* * * * *